Oct. 11, 1966 C. H. FISCHER Plant Pat. 2,677
GLADIOLUS PLANT
Filed Sept. 7, 1965
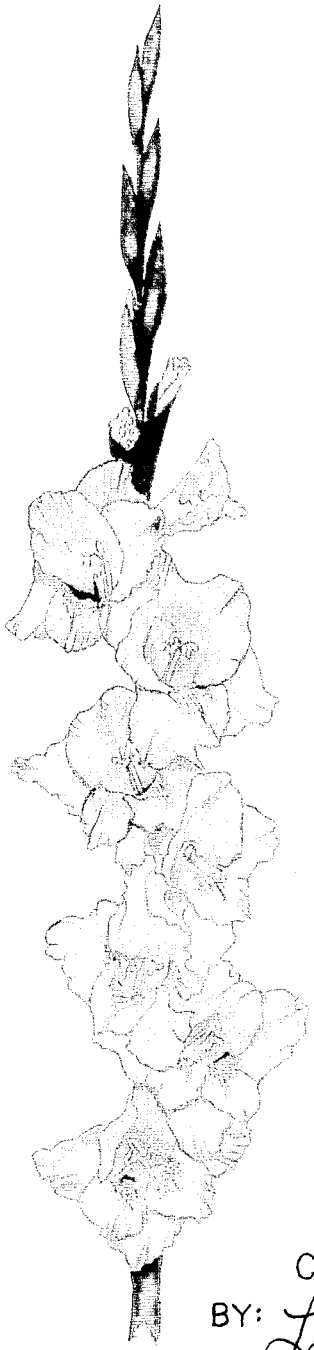
INVENTOR
Carl H. Fischer
BY: Lamont Johnston
ATTORNEY

United States Patent Office

Plant Pat. 2,677
Patented Oct. 11, 1966

2,677

GLADIOLUS PLANT

Carl H. Fischer, St. Charles, Minn., assignor to Selected Glads, Inc., New Albany, Ind., a corporation of Tennessee

Filed Sept. 7, 1965, Ser. No. 485,658
1 Claim. (Cl. Plt.—85)

My new invention relates to a new and improved variety of gladiolus and is notable particularly for a bright, blue-violet blotch in its blossom, its petite size and very straight spikes. I have identified this new variety as seedling #409–55 in my breeding work.

To the best of my knowledge, this variety is the result of a cross between Crusader (unpatented) and Caribbean (Plant Patent No. 1,654), Crusader being the seed parent and Caribbean the pollen parent. Hand cross pollenization was done by me in my field at St. Charles, Minnesota, but no precaution was taken to prevent admixture by bees or insects.

This new variety has been asexually reproduced by me in Minnesota and California by natural increase from cormels through several generations and its characteristics have proven to be permanently fixed.

The illustration, made a part of this application, shows a single bloom spike, reduced in size, and is as nearly true to color as it is possible to depict. The illustration shows the blotch, frilling and spike formation.

In the following detailed description, color plate references are to "The Horticultural Colour Chart" by the British Colour Council. Where there are other references to color, the ordinary dictionary meanings of the terms are intended.

*The plant*

Growth: Average grower. Attains a height of 45 inches over-all. Rather slow propagator.

Blooming: Blooms in about 85 days from large bulbs.

Stems: Slender; diameter is ¼ inch. Stem is white above the bulb.

Foliage: Medium green. Leaf is 1¼ to 1½ inches wide. Plant foliage, excluding the flower spike, is 28 to 30 inches in height.

Disease resistance: Average resistance to disease.

Corms: Clean, well-husked, smooth. Flesh varies from ivory next to the basal scar to medium yellow.

*The flower*

Spike: Flowerhead is 18 inches high with 16 to 18 buds of which 6 open at one time.

Bud:

*Size.*—Opening buds are 1¾ inches long.

*Opening.*—4 show color at one time.

Flower:

*Arrangement.*—Placement is semi-formal.

*Size.*—Individual florets are 3¼ inches in diameter.

*Form.*—Quite round and slightly ruffled; some needle-pointing.

*Keeping qualities.*—Average opener from tight bud.

Petals:

*Shape.*—Round, frilled and creased at mid-ribs of some petals.

*Size.*—Upper petal is 1¾ inches across; lip petal, 1⅛ inches.

*Aspect.*—Average substance.

*Fragrance.*—None.

*Color.*—White with slight lavender flush coming out from throat on upper side petals. Blotch on lip petal is Methyl Violet $39/_2$. Broad line of bright rose bisects the blotch. Calyx is purple with deeper Methyl Violet below the lip. Reverse of the 3 upper petals have streak of Methyl Violet $39/_3$ radiating out from the calyx.

Reproductive organs:

*Stamens.*—White; purple pollen.

*Pistil.*—White.

*Comparisons*

My new variety resembles Little Gem (unpatented) more than any other variety but differs from it principally as follows:

(1) It is smaller in floret size.

(2) It has a bluer throat.

(3) It has a sharper contrast between the white floret and blue throat.

(4) It is a slower propagator.

(5) It is not as tall.

Having thus disclosed my invention, I claim:

The new and distinct variety of gladiolus plant, substantially as herein shown and described, characterized by the blue throat of its blossom and by its petite size.

No reference cited.

ABRAHAM G. STONE, *Primary Examiner.*

R. E. BAGWILL, *Assistant Examiner.*